United States Patent
Konieczynski

(10) Patent No.: US 6,183,478 B1
(45) Date of Patent: *Feb. 6, 2001

(54) TEMPORARY FIXATION DEVICE

(75) Inventor: David Konieczynski, Needham, MA (US)

(73) Assignee: DePuy Orthopaedics, Inc., Warsaw, IN (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/244,974

(22) Filed: Feb. 4, 1999

(51) Int. Cl.[7] .................................................. A61B 17/58
(52) U.S. Cl. ............................. 606/104; 606/61; 606/69
(58) Field of Search ........................ 606/104, 61, 69; 81/448, 451; 227/146

(56) References Cited

U.S. PATENT DOCUMENTS

| | | | |
|---|---|---|---|
| 4,537,185 | 8/1985 | Stednitz | 128/92 B |
| 4,653,481 | 3/1987 | Howland et al. | 128/69 |
| 4,836,196 | 6/1989 | Park et al. | 128/92 YM |
| 4,892,093 | 1/1990 | Zarnowski et al. | 606/82 |
| 5,062,850 | 11/1991 | MacMillan et al. | 623/17 |
| 5,098,435 | 3/1992 | Stednitz et al. | 606/73 |
| 5,102,412 | 4/1992 | Rogozinski | 606/61 |
| 5,129,909 | 7/1992 | Sutherland | 606/88 |
| 5,133,717 | 7/1992 | Chopin | 606/61 |
| 5,147,360 | 9/1992 | Dubousset | 606/61 |
| 5,180,381 | 1/1993 | Aust et al. | 606/61 |
| 5,234,431 | 8/1993 | Keller | 606/70 |
| 5,257,994 | 11/1993 | Lin | 606/61 |
| 5,300,073 | 4/1994 | Ray et al. | 606/61 |
| 5,324,291 | 6/1994 | Ries et al. | 606/71 |
| 5,334,204 | 8/1994 | Clewett et al. | 606/73 |
| 5,395,371 | 3/1995 | Miller et al. | 606/61 |
| 5,415,658 | 5/1995 | Kilpela et al. | 606/57 |
| 5,431,660 | 7/1995 | Burke | 606/104 |
| 5,496,321 | 3/1996 | Puno et al. | 600/61 |
| 5,527,314 | 6/1996 | Brumfield et al. | 606/61 |
| 5,534,001 | 7/1996 | Schlapfer et al. | 606/61 |
| 5,534,002 | 7/1996 | Brumfield et al. | 606/61 |
| 5,545,165 | 8/1996 | Biedermann et al. | 606/61 |
| 5,562,662 | 10/1996 | Brumfield et al. | 606/61 |
| 5,601,553 | 2/1997 | Trebing et al. | 606/61 |
| 5,616,144 | 4/1997 | Yapp et al. | 606/61 |
| 5,634,925 | 6/1997 | Urbanski | 606/61 |
| 5,674,244 | 10/1997 | Mathys | 606/208 |
| 5,716,356 | 2/1998 | Biedermann et al. | 606/61 |
| 5,741,252 | 4/1998 | Mazzio et al. | 606/54 |
| 5,741,268 | * 4/1998 | Schutz | 606/104 |
| 5,755,721 | 5/1998 | Hearn | 606/96 |
| 5,766,254 | 6/1998 | Gelbard | 623/17 |
| 5,904,685 | * 5/1999 | Walawalkar | 606/104 |

FOREIGN PATENT DOCUMENTS

WO 93/18716   9/1993   (WO) ........................... A61B 17/58

OTHER PUBLICATIONS

"New Additions: Cervical Spine Locking Plate System," SYNTHES Spine, October, 1995.

* cited by examiner

Primary Examiner—Michael Buiz
Assistant Examiner—Julian W. Woo
(74) Attorney, Agent, or Firm—Nutter, McClennen & Fish, LLP

(57) ABSTRACT

A device for temporarily affixing a bone plate to bone includes a sleeve, a bias member and a fixation member. The elongate, hollow sleeve has a proximal region and a distal region, and an inner diameter defined by openings at a proximal end and a distal end of the sleeve. The bias member is disposed within the sleeve in communication with the fixation member. The fixation member is at least partially disposed within the sleeve and has a proximal end and an at least partially-threaded distal, bone-engaging end. The fixation member moves longitudinally with respect to the sleeve such that a predetermined amount of the fixation member may extend beyond the distal end of the sleeve.

30 Claims, 3 Drawing Sheets

TEMPORARY FIXATION DEVICE

CROSS-REFERENCE TO RELATED APPLICATIONS

Not applicable.

STATEMENT REGARDING FEDERALLY-SPONSORED RESEARCH

Not applicable.

FIELD OF THE INVENTION

The invention relates generally to devices for affixing a component to bone, and more particularly, to a device for temporarily affixing a bone plate to two or more spinal vertebrae.

BACKGROUND OF THE INVENTION

Following fracture or surgical treatment of the spine, it is often necessary to attach or fix a bone plate to two or more spinal vertebrae via a screw assembly in order to stabilize the spine, to promote fusion, and to expedite mobilization of a patient. One difficult aspect of affixing a bone plate to the vertebrae is the positioning of surgical instruments and implant components within the surgical site. This difficulty is often attributable to the relatively high level of precision required during this surgical procedure.

The need for a relatively high level of precision is due to a number of factors. First, the surgical opening is usually only two or three inches long, which provides a limited field of vision for the surgeon, and limits freedom of movement within the surgical site. Second, the spine is a particularly sensitive and delicate part of the human body that does not lend itself to in-depth probing or exploration. Third, delicate soft tissue proximate the surgical site must be retracted during the surgery without being cut or perforated.

The requisite level of precision, however, is often difficult to achieve in view of the inability to know, in advance, the specific bone plate geometry required to provide optimal stability for the spine. Usually, several bone plates must be temporarily secured to vertebrae and subsequently removed from the surgical site before finding a proper bone plate geometry. But, each insertion and removal of a bone plate increases the likelihood of surgical imprecision.

A number of temporary fixation pins and screws have been developed that allegedly facilitate the temporary fixation of bone plates to two or more vertebrae. These prior art temporary fixation pins and screws, however, suffer from certain drawbacks. For example, a fixation screw is generally sharp enough to penetrate bone. This sharpness can easily damage tissue, however, given the delicate nature of the spine and the soft tissue encountered at the surgical site, coupled with the relatively narrow visual opening into the surgical site.

It would therefore be desirable to provide a device that facilitates the safe and precise temporary fixation of a bone plate to two or more spinal vertebrae.

SUMMARY OF THE INVENTION

The present invention provides a device for facilitating the temporary fixation of a bone plate to two or more spinal vertebrae. Although the invention is primarily shown and described as a device for temporarily affixing a bone plate to two or more spinal vertebrae, it is understood that the device has other applications as well.

The temporary fixation device includes a fixation member slidably disposed within a sleeve. The fixation member is movable with respect to the sleeve between retracted and extended positions. A bias member is disposed within the sleeve in communication with the fixation member for biasing the fixation member to a retracted position. As the fixation member moves from the retracted position to an extended position, a distal, bone-engaging end of the fixation member emerges from the sleeve. The distal end of the fixation member is at least partially threaded so as to penetrate and engage bone and to secure the bone plate to the vertebrae.

BRIEF DESCRIPTION OF THE DRAWINGS

A more complete understanding of the present invention and the attendant advantages and features thereof will be more readily understood by reference to the following detailed description when it is considered in conjunction with the accompanying drawings, wherein.

DETAILED DESCRIPTION OF THE INVENTION

The drawings are understood to be illustrative of the concepts disclosed herein to facilitate comprehension of the invention. Further, the drawings are not to scale, and the scope of the invention is not to be limited to the particular embodiments shown and described herein.

Figure 1:
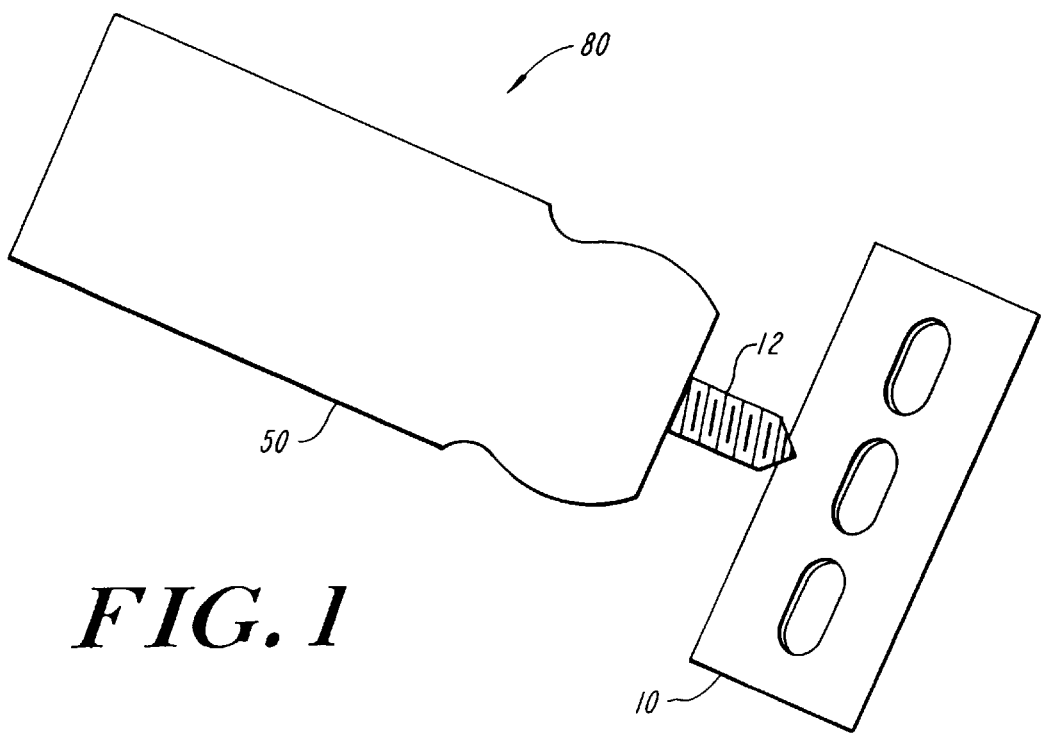
FIG. 1 is a perspective view of a device for providing temporary fixation of a bone plate to two or more vertebrae in accordance with the present invention.

FIG. 1 shows a device 80 for providing temporary fixation of a bone plate 10 to two or more vertebrae. The device 80 includes a fixation member 12, which is slidably disposed in a sleeve 50. The fixation member 12 is movable between a retracted position (FIG. 7) and an extended position (FIG. 8), as described in detail below. While in the retracted position, the sleeve 50 prevents the fixation member 12 from inadvertently damaging tissue. And, while in the extended position, the fixation member 12 can engage bone so as to secure the bone plate 10 to two or more vertebrae.

Figure 2:
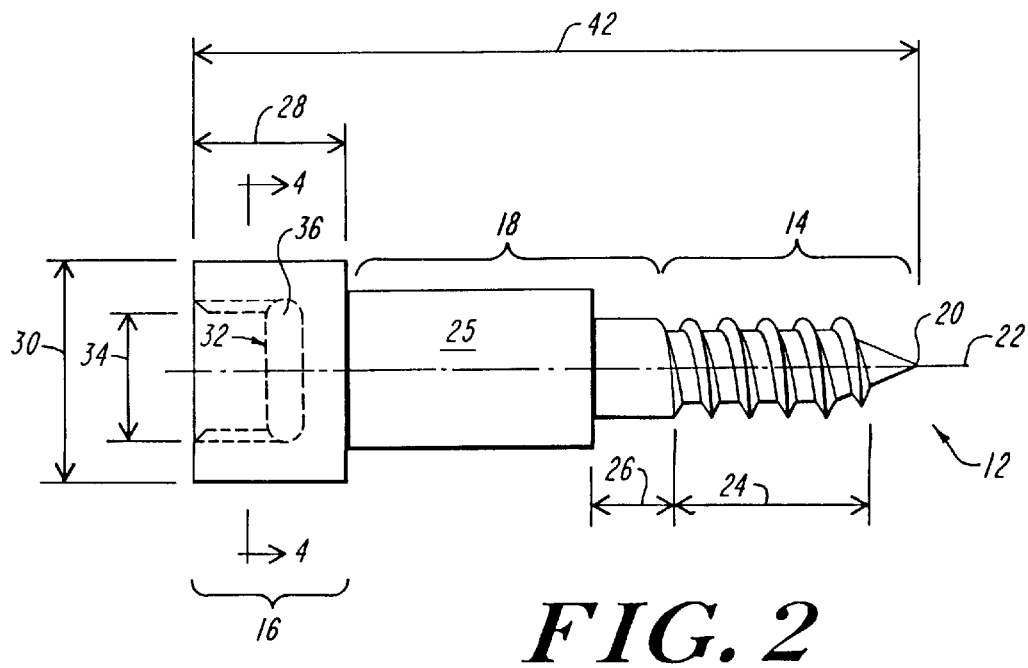
FIG. 2 is a side view of a temporary fixation member in accordance with the present invention.

FIG. 2 shows a fixation member 12, which includes a distal end 14 for penetrating and engaging bone and a proximal end 16 for coupling to a rotating member. A connection region 18 is located between the distal and proximal ends 14, 16 of the fixation member 12. The distal, bone-engaging end 14 of the fixation member 12 terminates at a sharp point 20 that approximately coincides with a longitudinal axis 22 of the fixation member. The distal, bone-engaging end 14 of the fixation member 12 has a threaded portion 24 with a predetermined pitch to allow for sufficient penetration and engagement of the fixation member 12 with bone. In one embodiment, the threaded portion 24 has a pitch and a quantity of threads sufficient to achieve self-tapping of the fixation member 12 into bone. In an exemplary embodiment, the threaded portion 24 of the distal, bone-engaging end 14 has at least four threads.

The fixation member 12 should be sized so as to occupy a volume less than or substantially equal to that of the permanent bone screw to be implanted in the bone plate. Specifically, the diameter of the distal, bone-engaging end 14 of the fixation member 12 should be less than or equal to the diameter to the distal end of the permanent bone screw in order to minimize the volume of bone removed during the process and, in turn, to optimize the attachment strength of the permanent bone screw.

The connection region 18 of the fixation member 12 is substantially cylindrical with a diameter that is greater than the diameter of the distal, bone-engaging end 14 of the fixation member. In the exemplary embodiment shown in FIG. 2, the connection region has a first transition portion 25 and a second transition portion 26. The first and second transition portions 25, 26 each have substantially constant diameters, the diameter of the first transition portion generally being greater than the diameter of the second transition portion. In alternate embodiments (not shown), the connection region 18 may be tapered or may have a uniform diameter throughout the first and second transition portions 25, 26.

The proximal end 16 of the fixation member 12 is substantially cylindrical and has a length 28 and a diameter 30. The diameter 30 of the proximal end 16 is substantially constant and should be greater than the diameter of the connection region 18 of the fixation member 12. The fixation member 12 is open at its proximal end 16, the proximal end having a mating surface 32 formed thereupon. In the exemplary embodiment shown in FIG. 3, the mating surface 32 is a cylindrical cavity that is defined by an inner diameter 34 and a distal surface 36. The inner diameter 34 of the cavity 32 is substantially constant, but, alternatively, may be tapered. One of ordinary skill in the art will readily appreciate that the mating surface 32 does not necessarily have to have a diameter.

Figure 3:
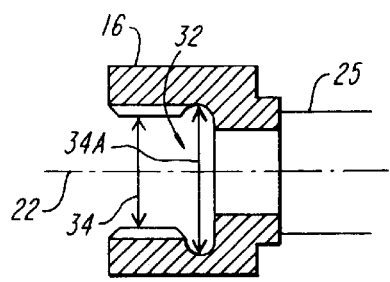
FIG. 3 is a side view of an inner portion of a proximal end of the temporary fixation member of FIG. 1.

Preferably, and as shown in FIG. 3, the distal surface 36 of the cavity 32 has a diameter 34A that is greater than that of the remainder of the inner diameter 34 of the cavity 32. This configuration facilitates the introduction, and subsequent retention, of a rotating member (not shown) in the cavity 32.

Figure 4:
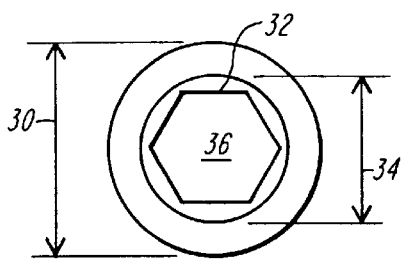
FIG. 4 is a cross-sectional view of a proximal end of the temporary fixation member of FIG. 1 taken along line 4—4.

FIG. 4 also shows the distal surface 36 of the mating surface 32. The distal surface 36 should be shaped to allow for coupling of the fixation member 12 to a rotating member (not shown), such as a universal driver. In the illustrated embodiment, the distal surface 32 is hex-slotted. One of ordinary skill in the art, however, will appreciate that the distal surface 32 may have a different shape besides hexagonal.

In the exemplary embodiment of the fixation member 12 shown in FIGS. 2–4, the fixation member 12 has a length 42 between about 0.4 inch and about 1.0 inch. The length 28 of the proximal end 16 of the fixation member 12 is between about 0.1 inch and about 0.2 inch. The length of the connection region 18 of the fixation member 12 is between about 0.2 inch and about 0.45 inch. And, the length of the distal end 14 of the fixation member 12 is between about 0.1 inch and about 0.35 inch.

Figure 5:
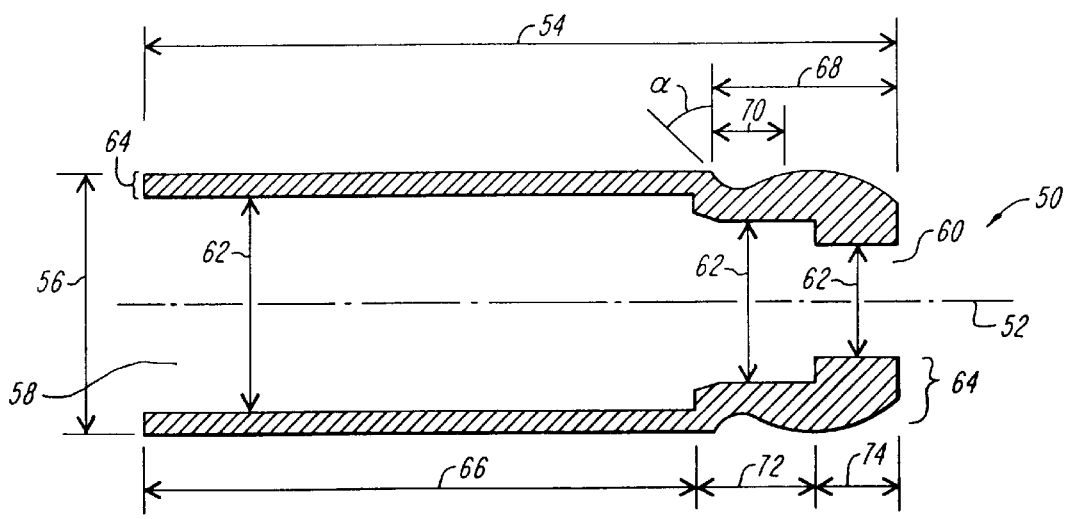
FIG. 5 is a side view of a sleeve in accordance with the present invention.

Referring now to FIG. 5, a sleeve in which the fixation member of FIGS. 2–4 may be disposed is shown. The sleeve 50 is elongate and substantially cylindrical and has openings at proximal and distal ends 58, 60 thereof, and an aperture therethrough. The sleeve 50 should have an inner diameter 62 and a length 54 such that the fixation member 12 has a predetermined range of longitudinal movement when disposed therein. The sleeve 50 also has a wall thickness 64, which is defined as the difference between an outer diameter 56 and the inner diameter 62 of the sleeve 50.

The sleeve 50 has a proximal region 66 which generally has substantially constant outer and inner diameters 56, 62. The proximal end 58 of the sleeve 50, however, may be provided with a rolled edge (not shown), or may have an outer diameter 56 that is smaller than the outer diameter 56 of the remainder of a proximal region 66 by a predetermined amount. This configuration is effective to retain the fixation member 12 of FIGS. 2–4 within the sleeve.

The sleeve 50 has a distal region 68 with a geometry such that the distal region may mate with a complimentary surface of a bone plate (not shown) and to allow placement of the sleeve at a variety of orientations. In one embodiment, the distal region 68 of the sleeve 50 is substantially spherical, with varying outer and inner diameters 56, 62.

The distal region 68 of the sleeve 50 has first and second areas 72, 74 each representing areas of reduced inner diameter 62 of the sleeve 50. The first area 72 is located proximal to the second area 74. In one embodiment, each of the first and second areas 72, 74 have substantially constant inner diameters 62, with the inner diameter of the first area 72 being greater than the inner diameter of second area 74. This configuration limits the amount of the fixation member 12 that may extend beyond the distal end 60 of the sleeve 50. One of ordinary skill in the art will appreciate that the inner diameters of either or both of the first and second areas 72, 74 need not be constant.

In an exemplary embodiment, the distal region 68 of the sleeve 50 also has a crimped portion 70 with a crimping angle a between about 30° and about 60°. Preferably, the crimped portion 70 reduces the outer diameter 56 of the first area 72 of the sleeve 50. Alternatively, the crimped portion 70 may reduce the outer diameter 56 of both the first and second areas 72, 74 of the distal region 68 of the sleeve, or solely the outer diameter of the second area of the distal region.

Figure 6:
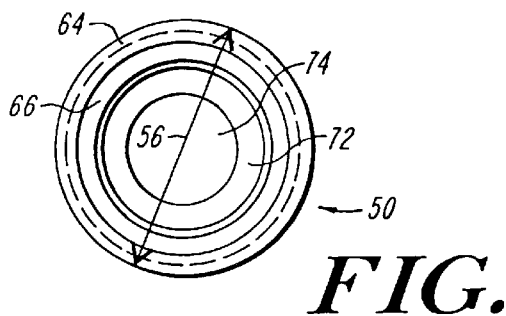
FIG. 6 is an end view from the proximal end of the sleeve of FIG. 5.

Referring now to FIG. 6, the various diameters of the sleeve 50 are shown. In this exemplary embodiment, the outer diameter 56 of the sleeve is greatest, followed by the inner diameter 62 at the proximal region 66, then the inner diameter at the first distal region 72 portion and then the inner diameter at the second area 74. FIG. 5 also depicts the wall thickness 64 of the sleeve 50.

The sleeve 50 has a longitudinal axis 52 and a length 54. The sleeve 50 has an exemplary length between about 0.4 inch and about 1.0 inch and is substantially cylindrical with a substantially constant outer diameter 56. The sleeve 50 may, however have a non-constant outer diameter 56; for example, the sleeve 50 may have a tapering outer surface diameter 56 such that the sleeve has a frustoconical shape.

Figure 7:
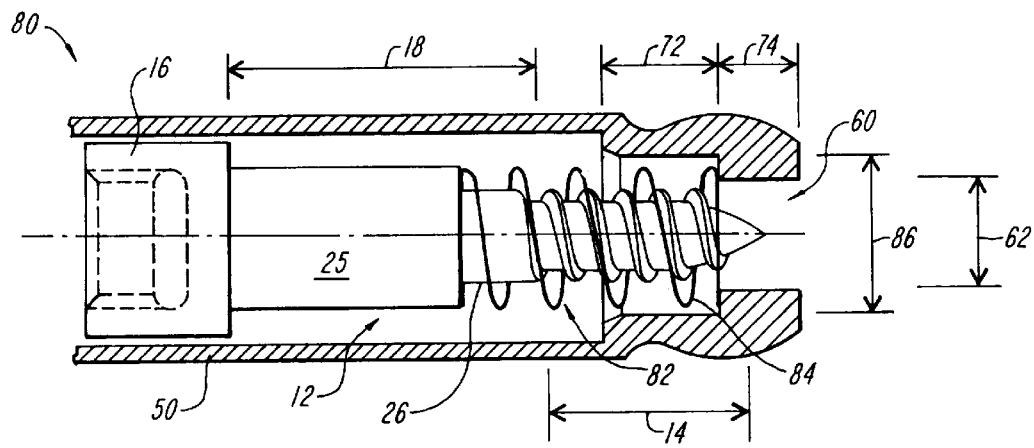
FIG. 7 is a partial sectional view of the temporary fixation device of FIG. 1 shown in a retracted position.

FIG. 7 shows the temporary fixation device 80 including a bias member 82 for biasing the fixation member 12 to a retracted position, as shown. In general, while in a retracted position, the bias member 82 should prevent the distal end 14 of the fixation member from extending beyond the sleeve 50.

In one embodiment, the bias member 82 is a spring having a plurality of coils 84 circumscribed about the distal, bone-engaging end 14 of the fixation member 12. The diameter 86 of the bias member 82 should be greater than the inner diameter 62 of the second area 74 of the fixation member 12 to prevent the bias member from exiting the distal end 60 of the sleeve 50. Further, the bias member 82 provides accuracy during the positioning of the fixation member 12 in bone, since the bias member surrounds the fixation member, thus not allowing the fixation member to drift within the sleeve 50.

Figure 8:
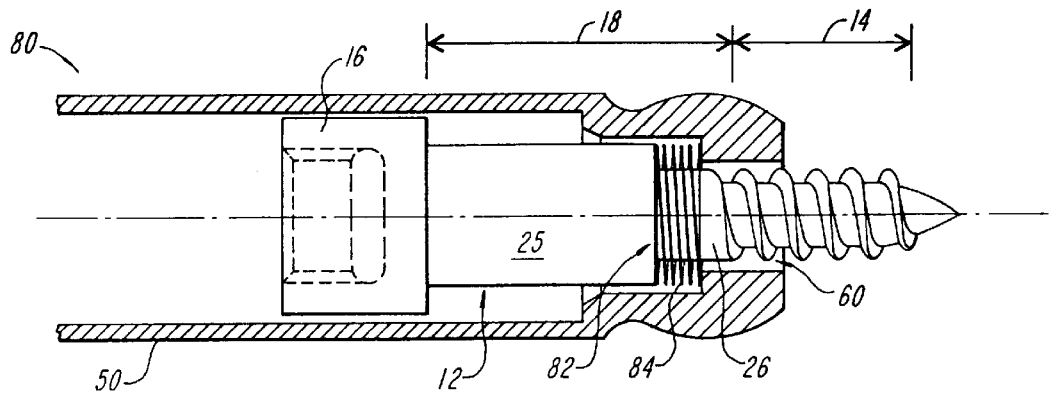
FIG. 8 is a partial sectional view of the temporary fixation device of FIG. 1 shown in an extended position.

FIG. 8 depicts device 80 with the fixation member 12 in an extended position. The extended position is characterized by the distal end 14 of the fixation member 12 extending beyond the distal end 60 of the sleeve 50. The specific length of the fixation member which extends beyond the sleeve 50 in the extended position can be readily varied.

In an exemplary embodiment of the temporary fixation device 80, the proximal end 16 of the fixation member 12 has a diameter which is greater than that of the first area 72 of the sleeve 50, to prevent it from being disposed therein. Also, the first transition portion 25 of the connection region 18 of the fixation member 12 should have a diameter greater than that of the second area 74 of the sleeve 50 to prevent it from being disposed therein.

Thus, the maximum amount of the fixation member 12 that may extend beyond the distal end 60 of the sleeve in this exemplary embodiment is equal to the length of the distal, bone-engaging end 14 of the fixation member 12 plus the length of the second transition portion 26 of the fixation member, minus the length of the second area 74 of the sleeve 50. This amount is generally between about 0.09 inch and about 0.39 inch.

One of ordinary skill in the art will readily appreciate, however, that because the first and second transition portions 25, 26 of the fixation may have a wide range of diameters, and/or may have equal diameters, that the amount of the fixation member that may extend beyond the distal end 60 of the sleeve may vary beyond the above range.

In use, the distal, bone-engaging end 14 of the fixation member 12 of the device 80 can be engaged with bone in several ways. By way of a non-limiting example, the distal, bone-engaging end 14 of the fixation member 12 can enter and engage bone through pre-drilled or already-fashioned holes. Preferably, the fixation member 12 is self-tapping.

Upon the removal of the distal end 14 of the fixation member 12 from bone, the bias member 82 automatically biases the fixation member to a retracted position in which the fixation member is disposed entirely within the sleeve 50 (see FIG. 7). This automatic biasing and retraction of the fixation member 12 into the sleeve 50 allows the surgeon, after removal of the fixation member 12 from bone, to move the device 80 within the surgical site with confidence that its sharp point 20 will not contact any vulnerable areas of the spine or surrounding soft tissue.

Figure 9:
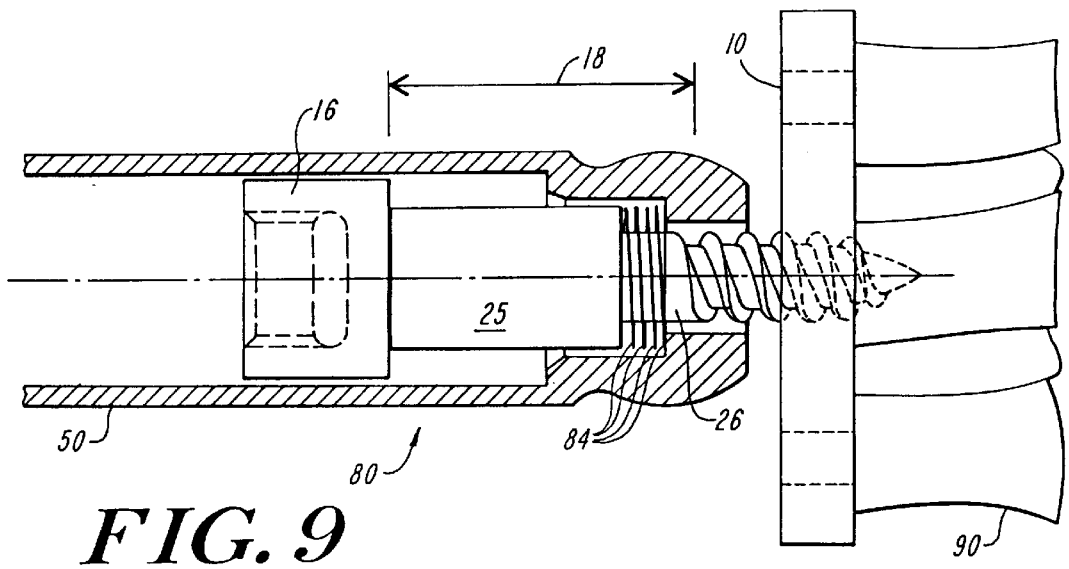
FIG. 9 is a partial sectional view of the temporary fixation device of FIG. 1 affixed to vertebrae.

FIG. 9 shows the device 80 affixed to vertebrae 90 through a bone plate 10. The device 80 can be affixed to vertebrae 90 either before or after a bone plate 10 has been suitably positioned on the vertebrae. Preferably, the bone plate 10 is positioned on the vertebrae 90 and then the device 80 is fit through the bone plate into the vertebrae. As described above, the device 80 may be fitted through a suitably-sized opening in the plate 10 and self-tapped or threaded into the vertebrae 90. This provides temporary fixation of the plate 10 to the vertebrae 90, the temporary fixation being maintained during subsequent surgical operations such as drilling, tapping operations. The device is then removed and replaced with permanent bone screws.

In a further embodiment (not shown) the device 80 includes a visual and/or aural indicator for indicating the amount of the fixation member 12 that extends beyond the distal end 60 of the sleeve 50.

Although the invention has been shown and described with respect to exemplary embodiments thereof, various other changes, omissions and additions in form and detail thereof may be made therein without departing from the spirit and scope of the invention. All references and publications cited herein are expressly incorporated herein by reference in their entirety.

What is claimed is:

1. A device for providing temporary fixation of a bone plate to two or more vertebrae, comprising:

an elongate sleeve having a proximal region and a distal region, each having an open end;

a fixation member for securing the plate to the vertebrae, the fixation member having a distal, bone-engaging end and a proximal end and being movable between a retracted position and an extended position, at least a portion of the distal, bone-engaging end of the fixation member extending beyond the distal end of the sleeve in the extended position; and a bias member coupled to the fixation member for biasing the fixation member to the retracted position.

2. The device of claim 1, wherein the distal, bone-engaging end of the fixation member has a threaded portion.

3. The device of claim 2, wherein the fixation member is self-tapping.

4. The device of claim 2, wherein the threaded portion of the distal, bone-engaging end of the fixation member has at least four full threads.

5. The device of claim 1, wherein the fixation member further includes:

a connection region located between the proximal and distal ends of the fixation member, the connection region having a diameter greater than a diameter of the distal, bone-engaging end but less than a diameter of the proximal end.

6. The device of claim 1, wherein the proximal end of the fixation member defines a mating surface.

7. The device of claim 6, wherein the mating surface is hex-slotted.

8. The device of claim 6, wherein the mating surface is a cylindrical cavity.

9. The device of claim 1, wherein the bias member surrounds the distal, bone-engaging end of the fixation member.

10. The device of claim 1, wherein the distal region of the sleeve further comprises:

a first area having a diameter less than a diameter of the proximal region of the sleeve; and a second area distal to the first area of the sleeve, the second area having a diameter less than the diameter of the first area.

11. The device of claim 1, wherein the distal region of the sleeve has a crimped portion.

12. A device for providing temporary fixation of a bone plate to two or more vertebrae comprising:

an elongate, substantially cylindrical sleeve having an inner diameter, a proximal region and a distal region, the proximal and distal regions each having an open end, the distal region having a first area distal to the proximal region and a second area distal to the first area, the inner diameter of the sleeve being greater at the proximal region than at the distal region and greater at the first area than at the second area;

a fixation member having a distal, bone-engaging end, a proximal end and a connection region therebetween, the distal end of the fixation member having a threaded portion, the fixation member being movable between a retracted position and an extended position, and the distal, bone-engaging end of the fixation member extending beyond the distal end of the sleeve in the extended position; and a bias member circumscribed about the fixation member for biasing the fixation member to the retracted position, the bias member surrounding at least the threaded portion of the distal, bone-engaging end of the fixation member.

13. The device of claim 12, wherein a diameter of the bias member is greater than the diameter of the second area, and the diameter of the proximal end of the fixation member is greater than the diameter of the first area, and the diameter of the connection region is less than the diameter of the first area but greater than the inner diameter of the second area.

14. The device of claim 12, wherein in the retracted position of the device, by the fixation member is entirely disposed within the sleeve, and in the extended position of the device, is by a predetermined length of the fixation member extends beyond the distal end of the sleeve.

15. The device of claim 14, wherein the longitudinal length of the fixation member that extends beyond the distal end of the sleeve when the device is in the extended position is between about 0.09 inch and about 0.39 inch.

16. The device of claim 12, wherein the threaded portion of the distal end of the fixation member has at least four full threads.

17. The device of claim 12, wherein the bias member is a spring.

18. The device of claim 14, wherein the proximal end of the fixation member defines a hex-slotted mating surface.

19. The device of claim 14, wherein the proximal end of the fixation member defines a mating surface that is a cylindrical cavity.

20. A device for providing temporary fixation of an implantable medical device to bone, comprising:

an elongate sleeve having a proximal region and a distal region, each having an open end;

a fixation member for securing the implantable medical device to bone, the fixation member having a distal, bone-engaging end and a proximal end and being movable between a retracted position and an extended position, at least a portion of the distal, bone-engaging end of the fixation member extending beyond the distal end of the sleeve in the extended position; and a bias member coupled to the fixation member for biasing the fixation member to the retracted position.

21. The device of claim 20, wherein the distal, bone-engaging end of the fixation member has a threaded portion.

22. The device of claim 21, wherein the fixation member is self-tapping.

23. The device of claim 21, wherein the threaded portion of the distal, bone-engaging end of the fixation member has at least four full threads.

24. The device of claim 20, wherein the fixation member further includes:

a connection region located between the proximal and distal ends of the fixation member, the connection region having a diameter greater than a diameter of the distal, bone-engaging end but less than a diameter of the proximal end.

25. The device of claim 20, wherein the proximal end of the fixation member defines a mating surface.

26. The device of claim 25, wherein the mating surface is hex-slotted.

27. The device of claim 25, wherein the mating surface is a cylindrical cavity.

28. The device of claim 20, wherein the bias member surrounds the distal, bone-engaging end of the fixation member.

29. The device of claim 20, wherein the distal region of the sleeve further comprises:

a first area having a diameter less than a diameter of the proximal region of the sleeve; and a second area distal to the first area of the sleeve, the second area having a diameter less than the diameter of the first area.

30. The device of claim 20, wherein the distal region of the sleeve has a crimped portion.

* * * * *

UNITED STATES PATENT AND TRADEMARK OFFICE
CERTIFICATE OF CORRECTION

PATENT NO. : 6,183,478 B1  Page 1 of 1
DATED : February 6, 2001
INVENTOR(S) : David Konieczynski It is certified that error appears in the above-identified patent and that said Letters Patent is hereby corrected as shown below:

<u>Column 7,</u>
Line 21, delete the word "by"
Line 24, delete the word "is by"

Signed and Sealed this

Seventeenth Day of December, 2002

JAMES E. ROGAN
*Director of the United States Patent and Trademark Office*